United States Patent
Brode

[11] 3,931,267
[45] Jan. 6, 1976

[54] SILYLATED BISPHENOL
[75] Inventor: George L. Brode, Somerville, N.J.
[73] Assignee: Union Carbide Corporation, New York, N.Y.
[22] Filed: July 31, 1974
[21] Appl. No.: 493,406

[52] U.S. Cl. ................................. 260/448.8 R
[51] Int. Cl.$^2$ ..... C07F 7/04; C07F 7/08; C07F 7/18
[58] Field of Search ............... 260/448.2 B, 448.8 R

[56] References Cited
UNITED STATES PATENTS

| | | | |
|---|---|---|---|
| 2,611,776 | 9/1952 | Speier .................... | 260/448.8 R X |
| 3,055,864 | 9/1962 | Kerschner ............... | 260/488.2 B X |
| 3,328,450 | 7/1967 | Plueddemann ........... | 260/448.8 R |
| 3,595,974 | 7/1971 | Lloyd et al. ............. | 260/448.2 B |

Primary Examiner—Paul F. Shaver
Attorney, Agent, or Firm—George A. Skoler

[57] ABSTRACT

The silane compounds of the instant invention can be represented by the formula:

wherein $a$ has a value of 0 to 2 inclusive; wherein $n$ is an integer of 1 or 2; wherein $m$ has a value of 0 to 1 inclusive and wherein the sum of $n + m$ is 2; and wherein X is a hydrolyzable group.

4 Claims, No Drawings

SILYLATED BISPHENOL

This invention relates to silylated bisphenol structures.

The silane compounds of the instant invention can be represented by the formula:

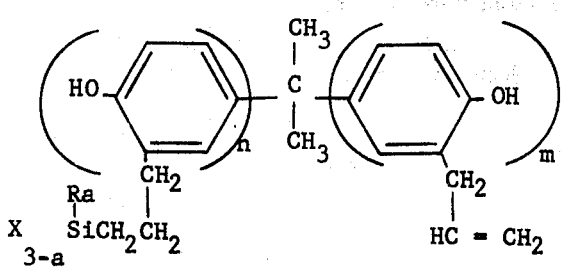

wherein $a$ has a value of 0 to 2 inclusive; wherein $n$ is an integer of 1 or 2; wherein $m$ has a value of 0 to 1 inclusive and wherein the sum of $n + m$ is 2; and wherein X is a hydrolyzable group.

Illustrative of hydrolyzable groups represented by X above are halo, such as chloro, bromo and fluoro, and alkoxy radicals having from 1 to 8 carbon atoms, such as methoxy, ethoxy, propoxy, butoxy, isobutyoxy, pentoxy, hexoxy, 2-chloro-propoxy, 2-chloroethoxy, and the like. Illustrative examples of such lower alkyl radicals represented by R above are methyl, ethyl, propyl and the like.

The functional silanes of the instant invention can be produced by the addition reaction of a silane containing silicon bonded hydrogen (i.e., silane hydride) of the formula

wherein X is as defined above with the unsaturated bisphenol-2,2-bis[4-hydroxy-3-allylphenyl]propane.

Illustrative of the more preferred silicon hydrogen containing silanes that can be employed are for example, trichlorosilane, tribromosilane, trifluorosilane, methyldichlorosilane, trimethoxysilane, triethoxysilane, tri-n-propoxysilane, methyldimethoxysilane, dimethylmethoxysilane, ethyldiethoxysilane, and the like.

The reaction between the silane hydrides and the unsaturated bisphenol can be effected by conventional addition reactions such as by the use of free radical addition catalysts, e.g., peroxide catalysts, or the platinum catalysts that are usually employed for such reactions, or with heat alone. Illustrative peroxide catalysts include for example, benzoyl peroxide, ditertiary-butyl peroxide, tertiary-butyl hydroperoxide and the like. Illustrative platinum catalysts include platinum metal, platinum deposited on a variety of particulate support materials such as charcoal, alumina, or silica particles. Particularly desirable is chloroplatinic acid. Usually, the amount of platinum catalysts employed ranges from about 5 to about 1,000 parts by weight of the catalyst per million parts by weight of the reactants.

The reaction may be effected in a solvent solution such as in hydrocarbon solvents, for example, normal hexane, octane, nonene, dodecane, benzene, toluene, xylene, mineral spirits, and the like, or halogenated hydrocarbons such as perchloroethylene, carbon tetrachloride, trifluoromethane, the arachlors, and the like. The reaction may be effected at any temperature sufficient to cause the addition of the silane to the unsaturated bisphenol. Minimum temperature is dependent on the catalyst chosen but usually the reaction proceeds from about room temperature to about 300°C. Most desirably the reaction is effected at about below about 250°C, and in the usual case at above about 40°C. The length of the reaction is dependent upon the degree of reaction desired and reaction periods ranging from seconds to days are contemplated and typical. The reaction is typical effected at ambient pressures, such as atmospheric pressure, but sub-atmospheric and super-atmospheric pressures can be employed though are not necessary.

Because the unsaturated bisphenol contains two unsaturated groups the stoichiometric amount of silane to that bisphenol will be in a molar ratio of 2 or less to 1. If it is desired to maintain in the resulting product some measurable amount of residual unsaturation, then the stoichiometry will be less than the 2 to 1 ratio. Using these guidelines one can produce all of the silane compositions depicted herein.

The silanes of this invention, because of their phenolic nature are eminently suitable as reactants in the formation of phenolic resins such as those based on the reaction of phenol and formaldehyde.

In addition, these silanes can be added to any variety of solid surfaces for which silane coupling agents have heretofore been employed. For example, the silanes can be used as coupling agents for the aforementioned polymers when they are reinforced or filled with particulate or fibrous materials such as, for example, the various siliceous particulate and pigmentary materials, as, for example, silica pigments of the hydrated, fumed, aerogels, xerogels, and the like varieties; the aluminum silicates such as the clay reinforcing fillers; alumina; iron oxide; brass coated steel fibers; glass fibers; foundry sands; iron, steel, aluminum, copper, silver, and the like metal surfaces, added for protection of such surfaces, as well as to provide a chemical coupling site, and the like. The silanes of this invention are particularly desirable in foundry resin applications where the resins are furfural-phenol, or urea-formaldehyde, or melamine-formaldehyde, all of which are acid cured at low temperatures, such as room temperature.

The following example is illustrative of the present invention and is not to be regarded as limiting.

A sample weighing 30.8 grams of 2,2-bis [4-hydroxy-3-(allyl)phenyl] propane $(n_D{}^{25} = 1.5853;$ % OH = 10.50) was dissolved in 250 ml. of toluene and all traces of water were removed by azeotropic distillation. Thereafter 0.43 gram of a 1 per cent solution of $H_2PtCl_6.6H_2O$ is dimethoxyethane was added to the dried solution and the mixture was stirred until a solution was formed. To this solution were added 24.4 grams of trimethoxysilane in 25 ml. of toluene. The resulting solution was maintained at about 260°C. for 5 hours and then heated at 65° to 75°C. for 3 hours. Infrared analysis showed that 2,2-bis[4-hydroxy-3-(gamma-trimethoxysilylpropyl) phenyl] propane was formed, immediately after silane addition.

Various modifications of this invention will be obvious to a worker skilled in the art and it is understood that such modifications and variations are to be included within the purview of this application and the spirit and scope of the claims.

What is claimed is:
1. A silane compound having the formula:
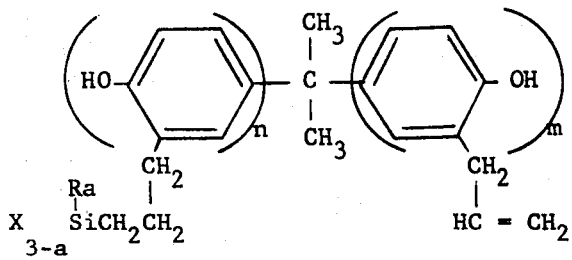
wherein R is a lower alkyl radical; $n$ is 1 or 2; $m$ is 0 or 1; the sum of $n + m$ is 2; $a$ is 0, 1 or 2; and X is a hydrolyzable group.
2. A silane compound as defined in claim 1, wherein $n$ is 2.
3. A silane compound as defined in claim 1, wherein X is a methoxy radical.
4. 2,2-bis[4-hydroxy-3-(gamma-trimethoxysilylpropyl)phenyl] propane.